United States Patent [19]

Wilson

[11] 4,309,440
[45] Jan. 5, 1982

[54] SUBSTITUTED BENZYLIDENE METHYLHYDRAZIDES OF ACETIC ACID, THEIR BACTERICIDAL AND FUNGICIDAL USE, AND METHOD OF PREPARATION

[75] Inventor: Charles A. Wilson, Pittsburg, Calif.

[73] Assignee: The Dow Chemical Company, Midland, Mich.

[21] Appl. No.: 210,996

[22] Filed: Nov. 28, 1980

[51] Int. Cl.$^3$ .................. A01N 37/28; A01N 37/34; C07C 109/08; C07C 121/82
[52] U.S. Cl. ................ 424/304; 260/465 D; 424/324; 564/151
[58] Field of Search .......... 260/465 D; 564/151; 424/304, 324

[56] References Cited

U.S. PATENT DOCUMENTS

| | | | |
|---|---|---|---|
| 3,055,938 | 9/1962 | Remy | 564/151 |
| 3,428,678 | 2/1969 | Trepanier | 564/149 |
| 3,481,972 | 12/1969 | Trepanier | 564/149 X |
| 3,746,703 | 7/1973 | Bruce | 564/151 X |
| 3,867,444 | 2/1975 | Baker | 564/209 |

*Primary Examiner*—Dolph H. Torrence
*Attorney, Agent, or Firm*—John M. Sanders

[57] ABSTRACT

Substituted benzylidene methylhydrazides of haloacetic acid corresponding to the formula

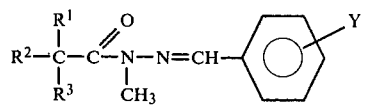

wherein $R^1$, $R^2$ and $R^3$ each independently represent hydrogen, chloro or bromo with the proviso that at least one of $R^1$, $R^2$ and $R^3$ is always chloro or bromo; Y represents hydrogen, chloro, bromo, nitro, or cyano. The compounds' use as antimicrobials and the method of preparing the same are also disclosed.

6 Claims, No Drawings

SUBSTITUTED BENZYLIDENE METHYLHYDRAZIDES OF ACETIC ACID, THEIR BACTERICIDAL AND FUNGICIDAL USE, AND METHOD OF PREPARATION

SUMMARY OF THE INVENTION

This invention relates to novel substituted benzylidene methylhydrazides of acetic acid corresponding to the formula

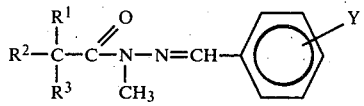

wherein $R^1$, $R^2$ and $R^3$ each independently represent hydrogen, chloro, or bromo, with the proviso that at least one of $R^1$, $R^2$ or $R^3$ is always chloro or bromo; Y represents hydrogen, chloro, bromo, nitro, or cyano. These compounds have utility as antimicrobial agents, especially in the kill and control or various bacterial and fungal organisms, such as, for example, *Staphylococcus aureus*, *Salmonella typhosa*, *Bacillus subtilis*, *Candida albicans* and *Candida pelliculosa*.

In the present specification and claims, the term "antimicrobial" as employed herein includes both the antibacterial and antifungal action of the compounds.

The compounds of the present invention can be prepared by the reaction of equimolar amounts of an appropriate benzylidene methylhydrazide and an appropriate haloacetyl halide in the presence of an organic solvent.

In carrying out this reaction, it is convenient to first prepare the benzylidene methylhydrazide reactant and then react it without purification with the haloacetyl halide reactant.

The benzylidene methylhydrazide reactant can be prepared by admixing a substituted benzaldehyde; an organic solvent, such as, for example, toluene, benzene or ethanol; and acetic acid and heating the resulting solution to a temperature of from about 25° C. to about 90° C., but preferably from about 40° C. to about 60° C., and then slowly adding the methylhydrazine reactant thereto. The water formed during the reaction is removed by conventional separatory procedures including decantation, evaporation and absorption with a dessicant and other such known procedures.

The benzylidene methylhydrazide thus prepared is then reacted, ordinarily without purification, with the haloacetyl halide at a temperature of from about 40° C. to about 60° C.

The above two step reaction can be characterized as follows:

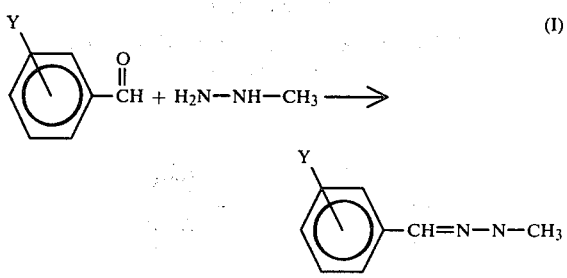

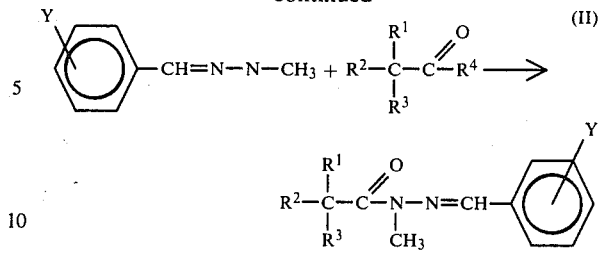

wherein $R^1$, $R^2$, $R^3$ and Y are as defined hereinbefore and $R^4$ is chloro or bromo. No attempt has been made to balance the above equations.

In carrying out the above two step reaction, it is convenient to have the reactants maintained under constant agitation during the reaction period. Depending on the specific reactants and solvents employed, the reaction is usually complete in from about ½ hour to about 12 hours. Upon completion of the reaction, the reaction mixture is cooled and the desired product (a solid) separated therefrom by filtration. Alternatively, the solvent is removed from the reaction mixture by evaporation and the product recovered as the residue. The product can be purified, if desired, by recrystallization from a solvent such as, for example, methanol.

When a bromoacetic acid is employed as the acetic acid source, it has been found that the reaction barely proceeds when ethanol is the solvent. It is preferred that ethanol not be used as a solvent when a bromoacetic acid is used.

DESCRIPTION OF SOME OF THE PREFERRED EMBODIMENTS

The following examples illustrate the present invention and the manner by which it can be practiced but, as such, should not be construed as limitations upon the overall scope of the same.

EXAMPLE 1

2-(4-chlorobenzylidene)-1-methylhydrazide chloroacetic acid

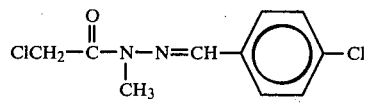

A 500 milliliter (ml) round bottom flask with magnetic stirring apparatus was charged with 250 ml of benzene, 28 grams (g) (0.2 moles) of 4-chlorobenzaldehyde and 2 ml of acetic acid. The solution was heated to about 40° C. and 10 g (0.2 moles) of methylhydrazine were slowly added thereto. The solution was heated to about 55°–60° C. and stirred for about one hour, after which the stirring was stopped. The mixture was allowed to cool and the water formed from the hydrazide formation was removed from the bottom of the flask with a suction pipette. The hydrazide solution was then treated with 22.6 g (0.2 moles) of chloroacetyl chloride. The mixture was slowly heated to about 50° C., and stirred for about one hour. The reaction mixture was then cooled and the solid product separated by filtration.

The 2-(4-chlorobenzylidene)-1-methylhydrazide chloroacetic acid was recovered as light yellow crystals in a yield of 10 g (20 percent of theoretical). The product melted at 169°–170° C. and upon analysis was found to have carbon, hydrogen, and nitrogen contents of 49.19, 4.10 and 11.52 percent, respectively, as compared to the theoretical contents of 49.00, 4.11 and 11.43 percent, respectively, calculated for the above-named structure.

EXAMPLE 2

2-(4-chlorobenzylidene)-1-methylhydrazide trichloroacetic acid

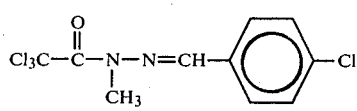

A 500 ml round bottom flask fitted with a magnetic stirrer was charged with 200 ml of benzene, about 1 ml of acetic acid, 14 g (0.1 mole) of 4-chlorobenzaldeyde, and 4.7 g (0.1 mole) of methylhydrazine. The flask was heated to about 50° C. and stirred for about one hour. The stirring was stopped and the water formed during the reaction was removed. The solution was dried with Na₂CO₃ crystals and filtered. A solution, containing 18.1 g (0.1 mole) of trichloroacetyl chloride dissolved in about 100 ml of benzene, was added over a 30 minute period to the reaction mixture. The solvent was removed via a rotary evaporator and the solid 2-(4-chlorobenzylidine)-1-methylhydrazide trichloroacetic acid product was recrystallized from methanol. The product was recovered in a yield of 17 g (55 percent of theoretical) and melted at 158°–159° C. Upon analysis the product was found to have carbon, hydrogen and nitrogen contents of 37.99, 2.59 and 9.09 percent, respectively, as compared to the theoretical contents of 38.25, 2.57 and 8.92 percent, respectively, calculated for the above-named structure.

By following substantially the preparative procedures as set forth above and employing the appropriate haloacetyl halide, the appropriately substituted benzaldehyde and methylhydrazine, the following compounds can be prepared.

EXAMPLE 3

2-(4-chlorobenzylidene)-1-methylhydrazide bromoacetic acid

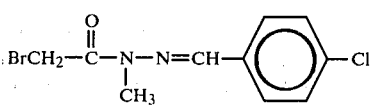

The above-named compound was recovered in a yield of 21 percent (6 g) of theoretical and melted at 150°–152° C. Upon analysis, the product was found to have carbon, hydrogen and nitrogen contents of 41.49, 3.51 and 9.81 percent, respectively, as compared to the theoretical contents of 41.47, 3.48 and 9.68 percent, respectively, calculated for the above-named structure.

EXAMPLE 4

2-(4-chlorobenzylidene)-1-methylhydrazide dichloroacetic acid

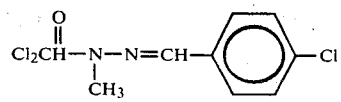

The above-named compound was recovered in a yield of 54 percent (30 g) of theoretical and melted at 145°–146° C. Upon analysis, the product was found to have carbon, hydrogen and nitrogen contents of 42.82, 3.11 and 10.03 percent, respectively, as compared to the theoretical contents of 42.96, 3.25, and 10.2 percent, respectively, calculated for the above-named structure.

EXAMPLE 5

2-(2-chlorobenzylidene)-1-methylhydrazide trichloroacetic acid

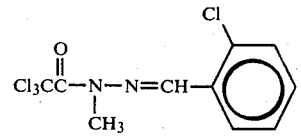

The above-named compound was recovered in a yield of 67 percent (26.4 g) of theoretical and melted at 186°–187° C. Upon analysis, the product was found to have carbon, hydrogen and nitrogen contents of 38.3, 2.76 and 9.08 percent, respectively, as compared to the theoretical contents of 38.25, 2.57 and 8.92 percent, respectively, calculated for the above-named structure.

EXAMPLE 6

2-(2-chlorobenzylidene)-1-methylhydrazide dichloroacetic acid

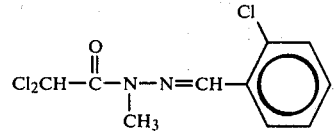

The above-named compound was recovered in a yield of 76 percent (26.6 g) of theoretical and melted at 174°–175° C. Upon analysis, the product was found to have carbon, hydrogen and nitrogen contents of 42.9, 3.29 and 10.22 percent, respectively, as compared to the theoretical contents of 42.92, 3.25 and 10.02 percent, respectively, calculated on the above-named structure.

EXAMPLE 7

2-(2-chlorobenzylidene)-1-methylhydrazide bromoacetic acid

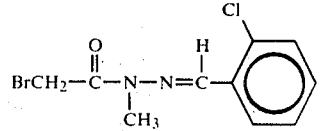

The above-named compound was recovered in a yield of 36 percent (13.2 g) of theoretical and melted at 114°–115° C. Upon analysis the product was found to have carbon, hydrogen and nitrogen contents of 41.2, 3.45 and 9.78 percent, respectively, as compared to the theoretical contents of 41.47, 3.48 and 9.69 percent, respectively, calculated on the above-named structure.

EXAMPLE 8

2-(2-chlorobenzylidene)-1-methylhydrazide chloroacetic acid

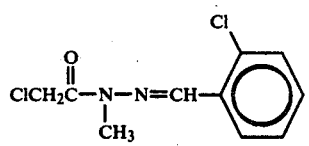

The above-named compound was recovered in a yield of 50 percent (15 g) of theoretical and melted at 134°–135° C. Upon analysis, the product was found to have carbon, hydrogen and nitrogen contents of 49.1, 4.18 and 11.54 percent, respectively, as compared to the theoretical contents of 49.0, 4.11 and 11.43 percent, respectively, calculated on the above-named structure.

EXAMPLE 9

2-(4-nitrobenzylidene)-1-methylhydrazide chloroacetic acid

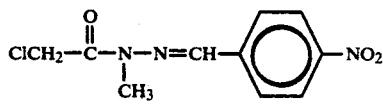

The above-named compound was recovered in a yield of 36 percent (4.5 g) of theoretical and melted at 217°–219° C. Upon analysis, the product was found to have 47.92, 4.01 and 16.93 percent, respectively, as compared to the theoretical contents of 46.98, 3.94 and 16.44 percent, respectively, calculated on the above-named structure.

EXAMPLE 10

Preparation of 2-(benzylidene)-1-methylhydrazide chloroacetic acid

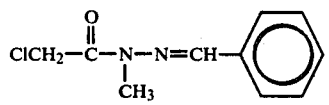

The above-named compound was recovered in a yield of 14 percent (3 g) of theoretical and melted at 143°–145° C. Upon analysis, the product was found to have carbon, hydrogen and nitrogen contents of 56.8, 5.46 and 13.45 percent, respectively, as compared to the theoretical contents of 57.01, 5.26 and 13.3 percent, respectively, calculated on the above-named structure.

EXAMPLE 11

2-(4-cyanobenzylidene)-1-methylhydrazide chloroacetic acid

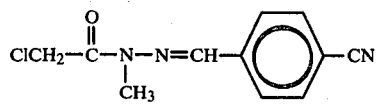

The above-named compound was recovered in a yield of 50 percent (6 g) of theoretical and melted at 150°–151° C. Upon analysis, the product was found to have carbon, hydrogen and nitrogen contents of 55.9, 4.75 and 19.62 percent, respectively, as compared to the theoretical contents of 56.06, 4.28 and 17.83 percent, respectively, calculated on the above-named structure.

EXAMPLE 12

2-(4-nitrobenzylidene)-1-methylhydrazide bromoacetic acid

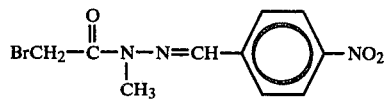

The above-named compound was recovered in a yield of 13 percent (2 g) of theoretical and melted at 203°–205° C. Upon analysis, the product was found to have carbon, hydrogen and nitrogen contents of 40.2, 3.43 and 14.23 percent, respectively, as compared to the theoretical contents of 40.02, 3.36 and 14.00 percent, respectively, calculated on the above-named structure.

EXAMPLE 13

2-(4-cyanobenzylidene)-1-methylhydrazide bromoacetic acid

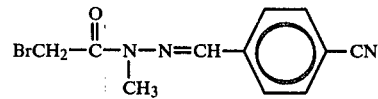

The above-named compound was recovered in a yield of 33 percent (6 g) of theoretical and melted at 165°–167° C. Upon analysis, the product was found to have carbon, hydrogen and nitrogen contents of 47.12, 3.74 and 15.10 percent, respectively, as compared to the theoretical contents of 47.16, 3.60 and 15.00 percent, respectively, calculated on the above-named structure.

EXAMPLE 14

2-(benzylidene)-1-methylhydrazide bromoacetic acid

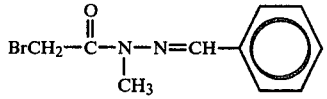

The above-named compound was recovered in a yield of 31 percent (8 g) of theoretical and melted at 95° C. Upon analysis, the product was found to have carbon, hydrogen and nitrogen contents of 46.9, 4.24 and 11.00 percent, respectively, as compared to the theoretical contents of 47.07, 4.35 and 10.98 percent, respectively, calculated on the above-named structure.

The infrared spectra of the compounds prepared in the above examples are consistent with the assigned structures.

In accordance with the present invention, it has been discovered that the substituted benzylidene methylhydrazides of haloacetic acid compounds can be employed for the control of many bacterial and fungal organisms. They can be applied to the aerial portions of many growing plants to control leaf-attacking fungal organisms or dispersed in soil or applied to plant seeds to control the root and seed attacking organisms of mold and damping off. In still other operations they can be applied to orchard floor surfaces to control over-wintering spores of many fungal organisms. In still further operations, the compounds of the invention or compositions containing them as toxic constituents can be included in and on plaster, ink, wallboard, textiles, paper adhesives, soaps, synthetic detergents, cutting oils, polymeric materials, embalming fluids, oil paints and latex paints to prevent the attack of various fungal organisms and the subsequent economic loss due to the degradation of such products by microorganisms. Also, the compounds can be distributed in textiles, cellulosic materials or in grain or can be employed in the impregnation of wood and lumber to preserve and protect such products from the attack of the organisms of rot, mold and decay.

The exact concentration of the toxicant to be employed in the treating compositions is not critical and may vary considerably provided the required dosage of the effective agent is supplied in the ink, adhesive soap, cutting oil, polymeric material, paint textile, paper, wood or growth medium or upon plant foliage. The concentration of toxicant in liquid compositions generally is from about 0.0000001 to 50 percent by weight. Concentrations up to 95 percent by weight are oftentimes conveniently employed, particularly in concentrate compositions. In dusts, the concentrations of the toxicant can be from about 0.1 to 95 percent by weight. In compositions to be employed as concentrates, the toxicants can be present in a concentration of from 5 to 98 percent by weight. For use as a foliar spray or in seed treatment, it is often convenient to apply the compounds as wettable powders.

In further embodiments, the compounds of the present invention or compositions containing the same, can be advantageously employed in combination wih one or more additional pesticidal compounds. Such additional pesticidal compounds may be insecticides, nematocides, arthropodicides, herbicides, fungicides or bactericides that are compatible with the compounds of the present invention in the medium selected for application and not antagonistic to the activity of the present compounds. Accordingly, in such embodiments, the pesticidal compound is employed as a supplemental toxicant for the same or for a different pesticidal use, or as an additament. The compounds in combination can generally be present in the ratio of from 1 to 100 parts of the compound of the present invention with from 100 to 1 parts of the additional compound(s).

In the following representative operations, the following abbreviations of microorganisms will apply:

| Abbreviation | Full Name |
| --- | --- |
| S. aur. | Staphylococcus aureus |
| S. ty. | Salmonella typhosa |
| B. sub. | Bacillus subtilis |
| C. alb. N. | Candida albicans NIH |
| C. alb. D. | Candida albicans D |
| C. pell. | Candida pelliculosa |
| Tor. | Torulopsis specie Med. Col. VI. |
| A. pull. | Aureobasidium pullulans |
| C. ips | Ceratocystis ips |
| Tm | Trychophyton mentagrophytes |
| Pen. ch. | Pencillium chrysogenum |
| P 42 | Trichoderm sp. madison P-42 |
| A. fum. | Aspergillus fumig. Med. Col. VI |
| A. nigr. | Asperigillus niger |

In the following representative operations a conventional in vitro agar Petri dish dilution test for determining antimicrobial activity against bacteria and fungi was employed.

In a representative operation, each of the following compounds when employed as the sole toxicant in an aqueous composition at a concentration of 0.5 parts by weight per million parts of the ultimate composition (hereinafter ppm) was found to give substantially complete kill and control of the corresponding organism:

2-(4-chlorobenzylidene)-1-methylhydrazide chloracetic acid: *A. fum*

2-(4-chlorobenzylidene)-1-methylhydrazide bromoacetic acid: *Tm*

In another operation, the following compounds were found to give substantially complete kill and control of the corresponding organisms when employed as the sole toxicant in an aqueous composition at a concentration of 1 ppm:

2-(4-chlorobenzylidene)-1-methylhydrazide chloroacetic acid: *Tm*

2-(4-nitrobenzylidene)-1-methylhydrazide chloroacetic acid: *Tor*

2-(benzylidene)-1-methylhydrazide chloroacetic acid: *A. fum*

In another operation, the following compounds were found to give substantially complete kill and control of the corresponding organisms when employed as the sole toxicant in an aqueous composition at a concentration of 5 ppm:

| | |
| --- | --- |
| 2-(4-chlorobenzylidene)-1-methylhydrazide chloroacetic acid: | C. alb n, A. pull., C. ips., Pen. ch., A. fum., |
| 2-(2-chlorobenzylidene)-1-methylhydrazide bromoacetic acid: | S. aur., S. ty., B. sub., C. pell. C. ips., Tm., Pen. ch., A. fum. |
| 2-(2-chlorobenzylidene)-1-methylhydrazide chloroacetic acid: | Tm. |
| 2-(4-nitrobenzylidene)-1-methylhydrazide chloroacetic acid: | C. alb. N, C. alb. D, C. pell., A. pull., C. ips., Tm., Pen. ch., A. fum., A. nigr. |
| 2-(benzylidene)-1-methylhydrazide chloroacetic acid: | Tm., Pen. ch. |
| 2(-4-cyanobenzylidene)-1-methylhydrazide chloroaceitc acid: | C. ips., Tm., Pen. ch., A. fum. |
| 2-(benzylidene)-1-methylhydrazide bromoacetic acid: | Tm., A. fum. |

In another operation, the following compounds were found to give substantially complete kill and control of the corresponding organisms when employed as the sole toxicant in an aqueous composition at a concentration of 10 ppm:

| | |
|---|---|
| 2-(4-chlorobenzylidene)-1-methyl-hydrazide chloroacetic acid: | C. ips. |
| 2-(4-chlorobenzylidene)-1-methyl-hydrazide bromoacetic acid: | C. alb. D., C. pell. |
| 2-(4-nitrobenzylidene)-1-methyl-hydrazide chloroacetic acid | P 42 |
| 2-(4-cyanobenzylidene)-1-methyl-hydrazide bromoacetic acid: | C. ips. |

In another operation, the following compounds were found to give substantially complete kill and control of the corresponding organisms when employed as the sole toxicant in an aqueous composition at a concentration of 50 ppm:

| | |
|---|---|
| 2-(4-chlorobenzylidene)-1-methyl-hydrazide bromoacetic acid: | Tor., P 42, A. nigr. |
| 2-(2-chlorobenzylidene)-1-methyl-hydrazide bromoacetic acid: | C. alb. N, C. alb. D, Tor., A. pull., A. nigr. |
| 2-(4-nitrobenzylidene)-1-methyl-hydrazide chloroacetic acid: | S. aur., |
| 2-(benzylidene)-1-methylhydrazide chloroacetic acid: | A. pull., C. ips., A. nigr. |
| 2-(4-cyanobenzylidene)-1-methyl-hydrazide chloroacetic acid: | C. pell., A. pull., A. nigr. |
| 2-(4-nitrobenzylidene)-1-methyl-hydrazide bromoacetic acid: | Tm. |
| 2-(4-cyanobenzylidene)-1-methyl-hydrazide bromoacetic acid: | S. aur., B. sub., C. pell., Tm., Pen. ch. A. fum. |
| 2-(benzylidene)-1-methylhydrazide bromoacetic acid: | C. alb. N, C. alb. D, C. pell., Tor., A. pull., C. ips., Pen. ch., A. nigr. |

In another operation, the following compounds were found to give substantially complete kill and control of the corresponding organisms when employed as the sole toxicant in an aqueous composition at a concentration of 100 ppm:

| | |
|---|---|
| 2-(benzylidene)-1-methylhydrazide chloroacetic acid: | C. alb. N, C. alb. D |
| 2-(-4-(cyanobenzylidene)-1-methyl-hydrazide chloroacetic acid: | C. alb. N, C. alb. D |

In another operation, the following compounds were found to give substantially complete kill and control of the corresponding organisms when employed as the sole toxicant in an aqueous composition at a concentration of 500 ppm:

| | |
|---|---|
| 2-(4-chlorobenzylidene)-1-methyl-hydrazide trichloroacetic acid: | B. sub. |
| 2-(4-chlorobenzylidene)-1-methyl-hydrazide bromoacetic acid: | B. sub., S. aur. |
| 2-(4-chlorobenzylidene)-1-methyl-hydrazide dichloroacetic acid: | Tm. |
| 2-(2-chlorobenzylidene)-1-methyl-hydrazide chloroacetic acid: | S. aur., B. sub., A. fum. |
| 2-(4-nitrobenzylidene)-1-methyl-hydrazide chloroacetic acid: | B. sub. |
| 2-(benzylidene)-1-methylhydrazide chloroacetic acid: | S. aur., B. sub. |
| 2-(4-(cyanobenzylidene)-1-methyl-hydrazide chloroacetic acid: | S. aur., P 42 |
| 2-(4-nitrobenzylidene)-1-methyl-hydrazide bromoacetic acid: | C. pell., A. pull., C. ips., Pen. ch., A. fum. |
| 2-(4-cyanobenzylidene)-1-methyl-hydrazide bromoacetic acid: | S. ty., C. alb. N, C. alb. D, Tor., A. pull., A. nigr. |
| 2-(benzylidene)-1-methylhydrazide bromoacetic acid: | S. aur., B. sub., P 42 |

In another representative operation each of the following compounds when employed as the sole toxicant in an aqueous composition at a concentration of 500 ppm of the ultimate composition was found to inhibit the growth of the corresponding organisms:

| | |
|---|---|
| 2-(4-nitrobenzylidene)-1-methyl-hydrazide bromoacetic acid: | S. aur., B. sub. |
| 2-(benzylidene)-1-methylhydrazide bromoacetic acid: | S. ty. |

In another representative operation 2-(benzylidene)-1-methylhydrazide bromoacetic acid when employed as the sole toxicant in an aqueous composition at a concentration of 100 ppm of the ultimate composition was found to inhibit the growth of S. aur.

In another representative operation 2-(4-cyanobenzylidene)-1-methylhydrazide bromoacetic acid when employed as the sole toxicant in an aqueous composition at a concentration of 10 ppm of the ultimate composition was found to inhibit the growth of B. sub.

When applied at a dosage rate of from about 0.5 to about 500 parts per million, each of the compounds of the present invention, the utility of which is not specifically exemplifed above, has the ability to kill and control one or more of the hereinabove listed pests as well as other pests of the same class or classes.

STARTING MATERIALS

Bromoacetyl bromide, the various substituted chloroacetyl chloride and benzaldehydes, and methylhydrazide are all known materials which are available commercially.

I claim:

1. A substituted benzylidene methylhydrazide of acetic acid compound corresponding to the formula

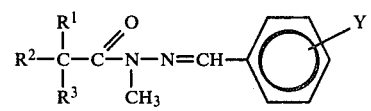

wherein $R^1$, $R^2$ and $R^3$ each independently represent hydrogen, chloro or bromo with the proviso that at least one of $R^1$, $R^2$ or $R^3$ is always chloro or bromo; Y represents hydrogen, chloro, bromo, nitro, or cyano.

2. The compound of claim 1 which is selected from the group consisting of 2-(4-chlorobenzylidene)-1-methylhydrazide chloroacetic acid, 2-(4-chlorobenzylidene)-1-methylhydrazide trichloroacetic acid, 2-(4-chlorobenzylidene)-1-methylhydrazide bromoacetic acid, 2-(4-chlorobenzylidene)-1-methylhydrazide dichloroacetic acid, 2-(2-chlorobenzylidene)-1-methylhydrazide trichloroacetic acid, 2-(2-chlorobenzylidene)-1-methylhydrazide dichloroacetic acid, 2-(2-chlorobenzylidene)-1-methylhydrazide bromoacetic acid, 2-(2-chlorobenzylidene)-1-methylhydrazide chloroacetic acid, 2-(4-nitrobenzylidene)methylhydrazide chloroacetic acid, 2-(4-2-(benzylidene)-1-methylhydrazide chloroacetic acid, 2-(4-cyanobenzylidene)-1-methylhydrazide chloroacetic acid, 2-(4-nitrobenzylidene)-1-methylhydrazide bromoacetic acid, 2-(4-cyanobenzylidene)-1-methylhydrazide bromoacetic acid and 2-(benzylidene)-1-methylhydrazide bromoacetic acid.

3. A method for the kill and control of bacteria and fungi which comprises applying to said bacteria and fungi or their habitat an antimicrobially effective amount of a substituted benzylidene methylhydrazide of acetic acid corresponding to the formula

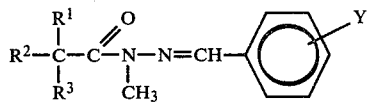

wherein $R^1$, $R^2$ and $R^3$ each independently represent hydrogen, chloro or bromo with the proviso that at least one of $R^1$, $R^2$ or $R^3$ is always chloro or bromo; Y represents hydrogen, chloro, bromo, nitro, or cyano in admixture with an inert adjuvant.

4. The method of claim 3 wherein the substituted benzylidene methylhydrazide of acetic acid is selected from the group consisting of 2-(4-chlorobenzylidene)-1-methylhydrazide chloroacetic acid, 2-(4-chlorobenzylidene)-1-methylhydrazide trichloroacetic acid, 2-(4-chlorobenzylidene)-1-methylhydrazide bromoacetic acid, 2-(4-chlorobenzylidene)-1-methylhydrazide dichloroacetic acid, 2-(2-chlorobenzylidene)-1-methylhydrazide trichloroacetic acid, 2-(2-chlorobenzylidene)-1-methylhydrazide dichloroacetic acid, 2-(2-chlorobenzylidene)-1-methylhydrazide bromoacetic acid, 2-(2-chlorobenzylidene)-1-methylhydrazide chloroacetic acid, 2-(4-nitrobenzylidene)methylhydrazide chloroacetic acid, 2-(4-2-(benzylidene)-1-methylhydrazide chloroacetic acid, 2-(4-cyanobenzylidene)-1-methylhydrazide chloroacetic acid, 2-(4-nitrobenzylidene)-1-methylhydrazide bromoacetic acid, 2-(4-cyanobenzylidene)-1-methylhydrazide bromoacetic acid and 2-(benzylidene)-1-methylhydrazide bromoacetic acid.

5. A method of preparing the substituted benzylidene methylhydrazides of acetic acid of claim 1 which comprises:
(a) admixing a substituted benzaldehyde of the formula

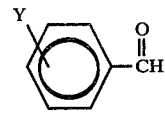

wherein Y represents hydrogen, chloro, bromo, nitro, or cyano in the presence of an organic solvent;
(b) with methylhydrazine, and then
(c) adding a haloacetyl halide of the formula

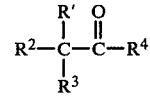

wherein $R^1$, $R^2$ and $R^3$ each represent hydrogen, chloro, or bromo with the proviso that at least one of $R^1$, $R^2$ or $R^3$ is always chloro or bromo; and $R^4$ represents chloro or bromo.

6. The method of claim 5 wherein the solvent is benzene, toluene or the proviso that ethanol not be used as the solvent when a bromoacetic acid compound is employed.

* * * * *

UNITED STATES PATENT AND TRADEMARK OFFICE
CERTIFICATE OF CORRECTION

PATENT NO. : 4,309,440
DATED : January 5, 1982
INVENTOR(S) : Charles A. Wilson

It is certified that error appears in the above—identified patent and that said Letters Patent is hereby corrected as shown below:

Col. 1, line 24, "or" should be --of--.

Col. 3, line 23, "chlorobenzaldeyde" should be --chlorobenzaldehyde--.

Col. 7, line 4, "are" should be --were--;
line 49, "wih" should be --with--.

Col. 8, line 14, "Asperigillus" should be --Aspergillus--;
line 62, "chloroaceitc" should be --chloroacetic--.

Col. 10, line 41, "exemplifed" should be --exemplified--.

Col. 12, line 37, --ethanol with-- should be added following the word "or".

Signed and Sealed this

Fourth Day of May 1982

[SEAL]

Attest:

GERALD J. MOSSINGHOFF

Attesting Officer    Commissioner of Patents and Trademarks